United States Patent
Rogovin et al.

(10) Patent No.: US 11,019,838 B2
(45) Date of Patent: Jun. 1, 2021

(54) PROBIOTIC DIETARY SUPPLEMENT FORMULATION

(71) Applicant: Jarrow Formulas, Inc., Los Angeles, CA (US)

(72) Inventors: Jarrow Rogovin, Los Angeles, CA (US); Peilin Guo, Manhattan Beach, CA (US)

(73) Assignee: Jarrow Formulas, Inc., Los Angeles, CA (US)

( * ) Notice: Subject to any disclaimer, the term of this patent is extended or adjusted under 35 U.S.C. 154(b) by 0 days.

(21) Appl. No.: 15/901,250

(22) Filed: Feb. 21, 2018

(65) Prior Publication Data

US 2018/0235271 A1 Aug. 23, 2018

Related U.S. Application Data

(60) Provisional application No. 62/461,375, filed on Feb. 21, 2017.

(51) Int. Cl.
| | |
|---|---|
| *A23L 33/135* | (2016.01) |
| *A61K 35/745* | (2015.01) |
| *A61K 47/14* | (2017.01) |
| *A61K 47/02* | (2006.01) |
| *A23L 33/115* | (2016.01) |
| *A23L 33/16* | (2016.01) |
| *A61K 47/22* | (2006.01) |
| *A61K 35/747* | (2015.01) |
| *A61K 35/744* | (2015.01) |

(52) U.S. Cl.
CPC ........... *A23L 33/135* (2016.08); *A23L 33/115* (2016.08); *A23L 33/16* (2016.08); *A61K 35/744* (2013.01); *A61K 35/745* (2013.01); *A61K 35/747* (2013.01); *A61K 47/02* (2013.01); *A61K 47/14* (2013.01); *A61K 47/22* (2013.01); *A23V 2002/00* (2013.01); *A23Y 2300/45* (2013.01)

(58) Field of Classification Search
CPC ...... A23L 33/135; A23L 33/115; A23L 33/16; A61K 35/747; A61K 35/744; A61K 35/745; A61K 47/14; A61K 47/02; A61K 47/22; A23Y 2300/45; A23V 2002/00
See application file for complete search history.

(56) References Cited

U.S. PATENT DOCUMENTS

| | | | |
|---|---|---|---|
| 4,518,696 A | 5/1985 | Gehrman et al. | |
| 8,460,726 B2 | 6/2013 | Harel et al. | |
| 8,871,266 B2 | 10/2014 | Crittenden et al. | |
| 9,107,429 B2 | 8/2015 | Wassell | |
| 9,301,982 B2 | 4/2016 | Lefkowitz | |
| 9,351,512 B2 | 5/2016 | Sjoberg | |
| 2003/0118571 A1* | 6/2003 | Reid | A61P 31/00 424/93.45 |
| 2004/0185032 A1* | 9/2004 | Burrell | A61K 35/745 424/93.45 |
| 2008/0254119 A1* | 10/2008 | Dai | A23L 33/16 514/1.1 |
| 2010/0074994 A1* | 3/2010 | Harel | A23L 3/40 426/61 |
| 2012/0171165 A1* | 7/2012 | Buck | A61K 31/702 514/23 |
| 2013/0087471 A1* | 4/2013 | Huber-Haag | B65D 77/22 206/205 |
| 2016/0270426 A1 | 9/2016 | Lerner | |

FOREIGN PATENT DOCUMENTS

| | | | |
|---|---|---|---|
| ES | 2422629 | * | 2/2012 |
| WO | WO 2014/195741 | * | 12/2014 |
| WO | WO2014195741 | * | 12/2014 |

OTHER PUBLICATIONS

National Institutes of Health "Health Information: Vitamin E" 11 pgs. 2013 (Year: 2013).*
Abe et al. "Safety Evaluation of Two Probiotic Bifidobacterial Strains, Bifidobacterium breve M-16V and Bifidobacterium infantis M-63, by Oral Toxicity Tests Using Rats" Bioscience Microflora vol. 28 (1), 7-15, 2009 (Year: 2009).*
Ishizeki et al. "Effect of administration of bifidobacteria on intestinal microbiota in low-birth-weight infants and transition of administered bifidobacteria: A comparison between one-species and three-species administration" Anaerobe 23 (2013) 38e44 (Year: 2013).*
Morinaga "Morinaga M-63, Bifidobacterium infantis" available online on Mar. 31, 2017 via Wayback Machine, 3pgs (Year: 2017).*
STN CAS Registry, "7664-38-2, Phosphoric acid, calcium salt, hydrate" 1 pg. accessed Jun. 7, 2020 (Year: 2020).*
Fujicalin, Product Information retrieved from http://www.fujicalin.com/product/, Accessed Nov. 28, 2016, 3 pages.
Maypro, Morinaga M-63 Product Information, retrieved from http://maypro.com/products/morinaga-m-63, Accessed Nov. 28, 2016, 2 pages.

* cited by examiner

Primary Examiner — Thane Underdahl
(74) Attorney, Agent, or Firm — Robinson & Cole LLP; John L. Cordani

(57) ABSTRACT

Dietary supplements comprising one or more probiotic bacteria or probiotic yeast in an oil with calcium phosphate added are provided. The calcium phosphate substantially reduces clumping and/or settling of the probiotic in oil. Other additives, such as anti-oxidants and taste enhancers, may be added to the compositions.

12 Claims, No Drawings

PROBIOTIC DIETARY SUPPLEMENT FORMULATION

This application claims priority under 35 U.S.C. § 119(e) to U.S. Provisional Patent Application No. 62/461,375 titled "Probiotic Dietary Supplement Formulation" filed on Feb. 21, 2017, the entire contents of which are hereby incorporated by reference.

FIELD OF THE INVENTION

The present invention relates to a formulation for dietary supplements comprising one or more probiotic bacteria or probiotic yeast in an oil with calcium phosphate added to substantially reduce clumping and/or settling of the probiotic powder in the oil.

BACKGROUND OF THE INVENTION

One of the roles of the intestinal microflora is to serve as a protective barrier, and inhibit the colonization of the intestines by pathogenic bacteria. Under normal conditions, the microflora in the intestines exist in a balanced ecosystem where beneficial microorganisms inhibit pathogens, support intestinal health and enhance immune response. This balanced ecosystem can be disrupted by the intake of antibiotics, unfavorable dietary composition, stress, or chronic conditions such as inflammation, obesity, etc., which can lead to overgrowth of pathogenic bacteria in the gut and cause a range of symptoms and conditions.

Probiotics are microorganisms that provide health benefits when consumed in a dietary supplement or through foods, whether a fermented food or by fortification. Probiotics inhibit pathogenic bacteria, help maintain a favorable gut environment, help strengthen the intestinal barrier and consequently help reduce the quantity of amines, putrabactive and other undesirable substances that can enter the system. Probiotics can also assist in restoring disrupted intestinal microflora, enhancing immune responses and inhibiting or clearing pathogens and their toxins. Lactic and acetic acid producing bacteria such as strains of *Lactobacillus* and *Bifidobacterium* are often used as probiotics in dietary supplements. They also produce short chain fatty acids, bacterocins and peptidoglycans that can benefit the host. Certain species of bacilli and yeasts are also used.

One problem encountered with probiotic formulations is stability during storage. One approach to address this problem is dispersing the probiotic in an oil, such as sunflower oil. While this can extend the shelf life of the probiotic formulation, the probiotic powder has a tendency to settle at the bottom of the container and clump with strong resistance to being re-suspended when shaken by hand. This can result in diminished or uneven dosages of probiotics being administered per unit volume of the oil and to material lost to use due to clumping. Accordingly, it would be desirable to have a formulation of probiotics mixed in an oil that resists settling and clumping of the probiotic powder.

SUMMARY OF THE INVENTION

The present invention is directed to a dietary supplement formulation comprising one or more strains of probiotic microorganisms mixed in an oil with calcium phosphate. The calcium phosphate substantially reduces clumping and settling of the probiotic in the oil when compared to probiotic powders in oil without calcium phosphate added.

Any lactic acid producing probiotic bacteria may be used in the dietary supplement formulation. For example, species and strains of *Lactobacillus* and *Bifidobacterium* may be used, as well as probiotic spore forming bacteria, such as *Bacillus coagulans*, or probiotic yeast, such as *Saccharomyces boulardii*. In one embodiment, the probiotic organism is *Bifidobacterium infantis* (*B. infantis*) and/or *Bifidobacterium breve* (*B. breve*). These probiotic species are particularly suitable in a dietary supplement for infants. These and other species of lactic acid producing probiotic bacteria may be used in formulations for older children and adults.

The oil used in the dietary supplement may be a vegetable oil, such as soybean oil, safflower oil, corn oil, palm oil, or canola oil, a mineral oil, or a coconut medium chain triglyceride oil. The calcium phosphate may be an anhydrous dibasic calcium phosphate, such as Fujicalin® dibasic calcium phosphate anhydrous sold by Fuji Chemical Industries.

Other additives or excipients can be added to the dietary supplement formulation. For example, an antioxidant, such as d-alpha-tocopherol, may be added to the dietary supplement formulation. Taste enhancers, such as citric acid, and other natural and artificial flavors may also be added to the dietary supplement formulation.

DETAILED DESCRIPTION OF THE INVENTION

The present disclosure provides improved compositions and methods for enhancing the shelf life and consistent administration of probiotics in dietary supplements. The dietary supplements of the present invention comprise one or more species and/or strains of probiotic bacteria, an oil and calcium phosphate. Other additives or ingredients, such as antioxidants and taste enhancers, may also be included.

In one embodiment, one or more strains of probiotic bacteria is mixed with an oil. Calcium phosphate is added to the mixture of probiotic bacteria and oil in order to substantially prevent settling and clumping of the probiotic bacteria in the oil. Any probiotic bacteria suitable for administration to humans may be used. For example the probiotic may be selected from genus of *Lactobacillus* and *Bifidobacterium*. The lactic acid producing bacterium that may be used include, but are not limited to, one or more of the following: *Bacillus subtilis, Bacillus coagulans, Bifidobacterium adolescentis, Bifidobacterium animalis, Bifidobacterium bifidum, Bifidobacterium breve, Bifidobacterium infantis, Bifidobacterium longum, Bifidobacterium thermophilum, Lactobacillus acidophilus, Lactobacillus agilis, Lactobacillus alactosus, Lactobacillus alimentarius, Lactobacillus amylophilus, Lactobacillus amylovorans, Lactobacillus amylovorus, Lactobacillus animalis, Lactobacillus batatas, Lactobacillus bavaricus, Lactobacillus bifermentans, Lactobacillus bifidus, Lactobacillus brevis, Lactobacillus buchnerii, Lactobacillus bulgaricus, Lactobacillus catenaforme, Lactobacillus casei, Lactobacillus cellobiosus, Lactobacillus collinoides, Lactobacillus confusus, Lactobacillus coprophilus, Lactobacillus coryniformis, Lactobacillus corynoides, Lactobacillus crispatus, Lactobacillus curvatus, Lactobacillus delbrueckii, Lactobacillus desidiosus, Lactobacillus divergens, Lactobacillus enterii, Lactobacillus farciminis, Lactobacillus fermentum, Lactobacillus frigidus, Lactobacillus fructivorans, Lactobacillus fructosus, Lactobacillus gasseri, Lactobacillus halotolerans, Lactobacillus helveticus, Lactobacillus heterohiochii, Lactobacillus hilgardii, Lactobacillus hordniae, Lactobacillus inulinus, Lactobacillus jensenii, Lactobacillus jugurti, Lactobacillus kandleri, Lactobacillus kefir, Lactobacillus lactis, Lactobacillus*

*leichmannii, Lactobacillus lindneri, Lactobacillus malefermentans, Lactobacillus mall, Lactobacillus maltaromicus, Lactobacillus minor, Lactobacillus minutus, Lactobacillus mobilis, Lactobacillus murinus, Lactobacillus pentosus, Lactobacillus plantarum, Lactobacillus pseudoplantarum, Lactobacillus reuteri, Lactobacillus rhamnosus, Lactobacillus rogosae, Lactobacillus tolerans, Lactobacillus torquens, Lactobacillus ruminis, Lactobacillus sake, Lactobacillus salivarius, Lactobacillus sanfrancisco, Lactobacillus sharpeae, Lactobacillus trichodes, Lactobacillus vaccinostercus, Lactobacillus viridescens, Lactobacillus vitulinus, Lactobacillus xylosus, Lactobacillus yamanashiensis, Lactobacillus zeae, Pediococcus acidilactici, Pediococcus pentosaceus, Streptococcus cremoris, Streptococcus diacetylactis, Streptococcus (Enterococcus) faecium, Streptococcus intermedius, Streptococcus lactis, Streptococcus thermophilus, Saccharomyces boulardii*, and combinations thereof.

The probiotic supplement may be formulated to provide between 1 million and 100 billion viable cells per serving, such as between 10 million and 10 billion viable cells per serving, or between 500 million and 2 billion viable cells per serving. In one embodiment, the dietary supplement contains about 1 billion viable cells per serving at the end of product shelf life. The probiotic microorganisms are mixed into the oil as a dried powder.

Examples of oils that may be used in the dietary supplement formulation include, but are not limited to, medium-chain triglycerides from such oils as coconut oil, soybean oil, safflower oil, corn oil, palm oil, canola oil, or other vegetable oils, mineral oils or combinations thereof.

Any form of calcium phosphate may be used in the dietary supplement formulation. An anhydrous form of calcium phosphate is desirable. In one embodiment, an anhydrous dibasic calcium phosphate is used. One example of an anhydrous calcium phosphate that may be used in the dietary supplement is Fujicalin® sold by Fuji Chemical Company.

An antioxidant, such as d-alpha-tocopherol, may be added to the oil. A taste enhancer, such as citric acid, may also be added. The invention is not limited in this regard, and any suitable antioxidant or taste enhancer may be added to the oil.

In some embodiments, the dietary supplement may comprise between about 85% to 95% by weight oil, between about 0.1% to 14.9% by weight of probiotic, and between about 0.1% to 3% by weight calcium phosphate. In one embodiment, the dietary supplement comprises about 94% by weight of a medium-chain triglyceride oil, about 5% by weight of probiotic, and about 1% by weight calcium phosphate. The dietary supplement may further include other additives or excipients, such as for example antioxidants and taste enhancers.

In one embodiment which is particularly suitable for infants, the probiotic supplement comprises *B. infantis*, *B. breve*, or combinations thereof. The probiotic dietary supplement may further include such other probiotic bacteria to which infants are exposed through the birth canal, during breast feeding and by environmental sources such as handling by the mother, nurses, family members or other persons. In this embodiment, the probiotic microorganisms are suspended in a medium-chain triglyceride oil. An anhydrous dibasic calcium phosphate is added to the supplement to prevent clumping of the probiotic microorganisms in the oil. Sufficient oil is provided to suspend and protect the *B. infantis* and *B. breve*. Citric acid is added to enhance taste of the dietary supplement.

A 0.5 ml serving of the dietary supplement for infants may comprise between about 20 to 30 mg of probiotic bacteria powder, between about 300 to 500 mg oil, between about 2 to 10 mg calcium phosphate, between about 0.05 to 0.3 mg of a tocopherol such as d-alpha-tocopherol, and between about 0.003 to 0.006 mg citric acid.

In one embodiment, the dietary supplement comprises the following ingredients in a 0.5 milliliter serving:
 about 25 mg *B. Infantis* M-63 (Moringa strain), providing 1 billion viable cells peer serving;
 about 488 mg medium chain triglyceride oil;
 about 5 mg calcium phosphate;
 about 0.9067 mg d-alpha-tocopherol; and
 about 0.005 mg citric acid.

The dietary supplement may be stored at room temperature for a period of up to 24 months without significant loss of viability of the probiotic microorganisms.

The probiotic, oil, calcium phosphate and any additional additives or excipients may be combined in any order. In one embodiment, the dietary supplement is made using the following process. An oil is mixed with calcium phosphate in a mixing vessel or tank. The probiotic is added to the oil and calcium phosphate mixture. The probiotic is typically in a dried powder form. Additional excipients, such as for example d-alpha-tocopherol and citric acid, may be added either before or after the probiotic. After mixing, the oil and probiotic mixture is discharged to a holding vessel. The holding vessel may have a nitrogen cover if desired to prevent exposure of the mixture to air or humidity. The oil and probiotic mixture is then transferred to bottles of a desired size.

As will be recognized by those of ordinary skill in the pertinent art based on the teachings herein, numerous changes and modifications may be made to the above-described and other embodiments of the invention without departing from its scope. Accordingly, this detailed description of preferred embodiments is to be taken in an illustrative as opposed to a limiting sense.

We claim:

1. A dietary supplement comprising an oil-based formulation, wherein:
 (a) one or more species or strains of probiotic bacteria; and
 (b) dibasic calcium phosphate are dispersed in an oil, in an amount that reduces clumping or settling of the probiotic compared to without the dibasic calcium phosphate.

2. The dietary supplement of claim 1, wherein the probiotic bacteria is selected from the group consisting of *Bacillus subtilis, Bacillus coagulans, Bifidobacterium adolescentis, Bifidobacterium animalis, Bifidobacterium bifidum, Bifidobacterium breve, Bifidobacterium infantis, Bifidobacterium longum, Bifidobacterium thermophilum, Lactobacillus acidophilus, Lactobacillus agilis, Lactobacillus alactosus, Lactobacillus alimentarius, Lactobacillus amylophilus, Lactobacillus amylovorans, Lactobacillus amylovorus, Lactobacillus animalis, Lactobacillus batatas, Lactobacillus bavaricus, Lactobacillus bifermentans, Lactobacillus bifidus, Lactobacillus brevis, Lactobacillus buchnerii, Lactobacillus bulgaricus, Lactobacillus catenaforme, Lactobacillus casei, Lactobacillus cellobiosus, Lactobacillus collinoides, Lactobacillus confusus, Lactobacillus coprophilus, Lactobacillus coryniformis, Lactobacillus corynoides, Lactobacillus crispatus, Lactobacillus curvatus, Lactobacillus delbrueckii, Lactobacillus desidiosus, Lactobacillus divergens, Lactobacillus enterii, Lactobacillus farciminis, Lactobacillus fermentum, Lactobacillus frigidus, Lactobacillus fructivorans, Lactobacillus fructosus, Lactobacillus gasseri, Lactobacillus halotolerans, Lactobacillus helveti-* cus, *Lactobacillus heterohiochii, Lactobacillus hilgardii, Lactobacillus hordniae, Lactobacillus inulinus, Lactobacillus jensenii, Lactobacillus jugurti, Lactobacillus kandleri, Lactobacillus kefir, Lactobacillus lactis, Lactobacillus leichmannii, Lactobacillus lindneri, Lactobacillus malefermentans, Lactobacillus mall, Lactobacillus maltaromicus, Lactobacillus minor, Lactobacillus minutus, Lactobacillus mobilis, Lactobacillus murinus, Lactobacillus pentosus, Lactobacillus plantarum, Lactobacillus pseudoplantarum, Lactobacillus reuteri, Lactobacillus rhamnosus, Lactobacillus rogosae, Lactobacillus tolerans, Lactobacillus torquens, Lactobacillus ruminis, Lactobacillus sake, Lactobacillus salivarius, Lactobacillus sanfrancisco, Lactobacillus sharpeae, Lactobacillus trichodes, Lactobacillus vaccinostercus, Lactobacillus viridescens, Lactobacillus vitulinus, Lactobacillus xylosus, Lactobacillus yamanashiensis, Lactobacillus zeae, Pediococcus acidilactici, Pediococcus pentosaceus, Streptococcus cremoris, Streptococcus diacetylactis, Streptococcus (Enterococcus) faecium, Streptococcus intermedius, Streptococcus lactis, Streptococcus thermophilus, Saccharomyces boulardii*, and combinations thereof.

3. The dietary supplement of claim 2, wherein the oil is selected from the group consisting of medium-chain triglycerides, soybean oil, safflower oil, corn oil, palm oil, canola oil, or other vegetable oils, mineral oils or combinations thereof.

4. The dietary supplement of claim 1, wherein the probiotic bacteria is *B. infantis, B. breve* or combinations thereof and the oil is a medium-chain triglyceride.

5. The dietary supplement of claim 4, further comprising d-alpha-tocopherol and citric acid.

6. The dietary supplement of claim 1, wherein the dietary supplement comprises between about 85% to 95% by weight oil, between about 1% to 14.5% by weight of probiotic, and between about 0.5% to 3% by weight dibasic calcium phosphate.

7. The dietary supplement of claim 5, wherein a 0.5 ml serving consists essentially of between about 20 to 30 mg of probiotic bacteria powder, between about 300 to 500 mg oil, between about 2 to 5 mg dibasic calcium phosphate, between about 0.05 to 0.3 mg of a tocopherol, and between about 0.003 to 0.006 mg citric acid.

8. The dietary supplement of claim 5, wherein a 0.5 ml serving consists essentially of:
about 25 mg *B. infantis* M-63 (Moringa strain), providing 1 billion viable cells per serving;
about 488 mg medium chain triglyceride oil;
about 5 mg dibasic calcium phosphate;
about 0.1 mg d-alpha-tocopherol;
and about 0.005 mg citric acid.

9. The dietary supplement of claim 1, wherein the dibasic calcium phosphate substantially reduces clumping and settling of the probiotic in the oil when compared to probiotic powders in oil without dibasic calcium phosphate added.

10. The dietary supplement of claim 1, wherein the dibasic calcium phosphate is anhydrous.

11. The dietary supplement of claim 1, wherein the probiotic bacteria is suspended in a medium-chain triglyceride oil.

12. The dietary supplement of claim 1, wherein the dietary supplement is non-aqueous.

\* \* \* \* \*